(12) United States Patent
Wagner

(10) Patent No.: US 7,319,017 B2
(45) Date of Patent: Jan. 15, 2008

(54) MONITORING HEART FAILURE

(75) Inventor: Daniel R. Wagner, Bertrange (LU)

(73) Assignee: Centre de Recherche Public de la Santé, Luxembourg (LU)

( * ) Notice: Subject to any disclaimer, the term of this patent is extended or adjusted under 35 U.S.C. 154(b) by 0 days.

(21) Appl. No.: 11/181,675

(22) Filed: Jul. 13, 2005

(65) Prior Publication Data

US 2006/0029993 A1    Feb. 9, 2006

Related U.S. Application Data

(63) Continuation-in-part of application No. PCT/EP2004/008259, filed on Jul. 23, 2004.

(51) Int. Cl.
    C12Q 1/37    (2006.01)
(52) U.S. Cl. .......................... 435/23; 435/810
(58) Field of Classification Search ...................... None
    See application file for complete search history.

(56) References Cited

U.S. PATENT DOCUMENTS 6,607,894 B1    8/2003    Lopata et al.

FOREIGN PATENT DOCUMENTS

| WO | WO97/38314 | 10/1997 |
|----|------------|---------|
| WO | WO 00/20860 | 4/2000 |
| WO | WO 02/89656 | 4/2002 |

OTHER PUBLICATIONS

Inokubo et al, "Plasma levels of matrix metalloproteinase-9 and tissue inhibitor of metalloproteinase-1 are increased in the coronary circulation in patients with acute coronary syndrome," (American Heart Journal), 2001, vol. 141, pp. 211-217.*
Creemers et al, "Matrix Metalloproteinase Inhibition After Myocardial Infarction: A New Approach to Prevent Heart Failure?" (Circulation Research), 2001, vol. 89, pp. 201-210.*
McLaren et al, "Prostaglandin E2-dependent Production of Latent Matrix Metalloproteinase-9 In Cultures Of Human Fetal Membranes," (Molecular Human Reproduction), 2000, vol. 6, No. 11, pp. 1033-1040.*
Altieri, P. (2003) "Metalloproteinases 2 & 9 are increased in plasma of patients with heart failure" *European Journal of Clinical Investigation*, 33, 648-656.
Blankenberg, Stefan et al. (2003) "Plasma Concentrations and Genetic Variations of Matrix Metalloproteinase 9 and Prognosis of Patients with Cardiovascular Disease" *Circulation*, 107: 1579-1585.
Bueb, Jean-Luc "Increased Levels of Matrix Metalloproteinase-9 in Patients with Acute Myocardial Infarction: No Correlation with C-Reactive Protein" ABSTRACTS-Myocardial Ischemia and Infarction.
Cleutjens, Jack P.M. & Creemers, Esther, EJM (2002) "Integration of Concepts: Cardiac Extracellular Matric Remodeling After Myocardial Infarction" *Journal of Cardiac Failure*, 8(6): S344-S348.

Ducharme, Anique, et al. (2000) "Targeted deletion of matrix metalloproteinase-9 attenuates left ventricular enlargement and collagen accumulation after experimental myocardial infarction" *The Journal of Clinical Investigation*, 106(1): 55-62.
Galis, Zorina S. & Khatri, Jaikirshan J. (2002) "Matrix Metalloproteinases in Vascular Remodeling and Atherogenesis" *Circ Res.* 90:251-262.
Galt, Spencer W. et al. (2001) "Differential Regulation of Matrix Metalloproteinase-9 by Monocytes Adherent to Collagen and Platelets" *Circ Res.*, 89: 509-516.
Inokubo, Yoichi et al. (2001) "Plasma levels of matrix metalloproteinase-9 and tissue inhibitor of metalloproteinase-1 are increased in the coronary circulation in patients with acute coronary syndrome" *American Heart Journal*, 141: 211-217.
Jugdutt, Bodh (2006) "Matrix Metalloproteinases as Markers of Adverse Remodeling After Myocardial Infarction" *Journal of Cardiac Failure* 12(1):73-76.
Jugdutt, Bodh (2003) "Ventricular Remodeling After Infarction and the Extracellular Collagen Matrix" *Circulation*, 108:1395-1403.
Kai, Hisashi, et al (1998) "Peripheral Blood Levels of Matrix Metalloproteases-2 and -9 Are Elevated in Patients with Acute Coronary Syndromes" *JACC*, 32(2): 236-372.
Lehoux, Stephanie, et al. (2004) "Pressure-Induced Matrix Metalloproteinase-9 Contributes to Early Hypertensive Remodeling" *Circulation*, 109: 1041-1047.
Li, Yun You et al. (2000) "Interplay of matrix metalloproteinases, tissue inhibitors of metalloproteinases and their regulators in cardiac matrix remodeling" *Cardiovascular Research* 46: 214-224.
Li, Yun You et al. (2002) "MMP inhibition modulates TNF-α transgenic mouse phenotype early in the development of heart failure" *Am. J Physiol Heart Circ Phusiol* 282: H983-H989.
Li, Yun You et al. (1998) "Differential Expression of Tissue Inhibitors of Metalloproteinases in the Failing Human Heart" *Circulation*, 98: 1728-1734.
Libby, Peter and Lee, Richard T. (2000) "Matrix Matters" *Circulation*, 102:1874-1876.
Mann, Douglas L. (2002) "Tumor Necrosis Factor-Induced Signal Transduction and Left Ventricular Remodeling" *Journal of Cardiac Failure*, 8(6): S379-S386.

(Continued)

Primary Examiner—Ralph Gitomer
Assistant Examiner—Amanda P. Wood
(74) Attorney, Agent, or Firm—Quine Intellectual Property Law Group, P.C.

(57) ABSTRACT

An in vitro method for identifying subjects at risk of heart failure following a Myocardial Infarction comprising analyzing the concentration of Matrix Metalloproteinase-9 in a bodily sample from a subject who has suffered a Myocardial Infarction and comparing this concentration with a reference for concentrations of Matrix Metalloproteinase-9 in individuals who have not suffered a Myocardial Infarction; wherein a raised concentration of Matrix Metalloproteinase-9 in the bodily sample from a subject who has suffered a Myocardial Infarction suggests the subject is at risk of heart failure.

10 Claims, 3 Drawing Sheets

OTHER PUBLICATIONS

Manolio, Teri (2003) "Novel Risk Markers and Clinical Practice" *N Engl J Med*, 349(17): 1587-1589.

Mukherjee, Rupak et al. (2003) "Myocardial Infarct Expansion and Matrix Metalloproteinase Inhibition" *Circulation*, 107: 618-625.

Nian, Min et al. (2004) "Inflammatory Cytokines and Postmyocardial Infarction Remodeling" *Circ Res.*, 94: 1543-1553.

Oak, Min-Ho et al. (2004) "Red Wine Polyphenolic Compounds Strongly Inhibit Pro-Matrix Metalloproteinase-2 Expression and Its Activation in Response to Thrombin via Direct Inhibition of Membrane Type 1-Matrix Metalloproteinase in Vascular Smooth Muscle Cells" *Circulation*, 110: 1861-1867.

Pitt, Geoffrey "Matrix Metalloproteinases Are Molecules of the Moment" theheart.org, Sep 13, 2000 14:18:47.

Reinhardt, D. et al. (2002) "Cardiac remodeling in end stage heart failure: upregulation of matrix metalloproteinase (MMP) irrespective of the underlying disease, and evidence for a direct inhibitory effect of ACE inhibitors in MMP" *Heart*, 88:525-530.

Renko, J. et al. (2004) "Serum matrix metalloproteinase-9 is elevated in men with a history of myocardial infarcation" *Scand. J. Clin Lab Invest*, 64: 255-262.

Reynolds, Mark A. et al. (2003) "Early Biomarkers of Stroke" *Clinical Chemistry* 49(10): 1733-1739.

Romanic, Anne M., et al. (2002) "Myocardial protection form ischemia/reperfusion injury by targeted deletion of matrix metalloproteinase-9" *Cardiovascular Research*, 54:549-558.

Shiomi, Tetsuya et al. (2004) "Overexpression of Glutathione Peroxide Prevents Left Ventricular Remodeling and Failure After Myocardial Infarction in Mice" *Circulation*, 109:544-549.

Spinale, Francis G. (2002) "Matrix Metallopoteinases: Regulation and Dysregulation in the Failing Heart" *Circ Res.* 90:520-530.

Spinale, Francis G. (2002) "Bioactive Peptide Signaling Within the Myocardial Interstitium and the Matrix Metalloproteinases" *Circ Res.* 91:1082-184.

Squire, Iain B. et al. (2004) "Plasma MMP-9 and MMP-2 Following Acute Myocardial Infarction in Man: Correlation with Echocardiographic and Neurohumoral Parameters of Left Ventricular Dysfunction" *Journal of Cardiac Failure*, 10(4): 328-333.

Sundström, Johan et al. (2004) "Relations of Plasma Matrix Metalloproteinase-9 to Clinical Cardiovascular Risk Factors and Echocardiographic Left Ventricular Measures" *Circulation*, 109: 2850-2856.

Thompson, Matt M. and Squire, Iain B. (2002) "Matrix metalloproteinase-9 expression after myocardial infarction: physiological or pathological?" *Cardiovascular Research*, 54: 495-498.

Tsuruda, Toshihiro, et al. (2002) "Brain Natriuretic Peptide Is Produced in Cardiac Fibroblasts and Induces Matrix Metalloproteinases" *Circ. Res.*, 91: 1127-1134.

Wagner, et al. (2006) "Matrix Metalloproteinase-9 Is a Marker of Heart Failure After Acute Myocardial Infarction" *Journal of Cardiac Failure*, 12(1):66-72.

Wilson, Eric M. et al. (2003) "Region- and Type-Specific Induction of Matrix Metalloproteinases in Post-Myocardial Infarction Remodeling" *Circulation*, 107: 2857-2863.

Wilson, Eric M. et al. (2002) "Plasma Matrix Metalloproteinase and Inhibitor Profiles in Patients with Heart Failure" *Journal of Cardiac Failure*, 8(6):390-398.

Yarbrough, William M. et al. (2003) "Selective Targeting and Timing of Matrix Metalloproteinase Inhibition in Post-Myocardial Infarction Remodeling" *Circulation*, 108:1753-1759.

\* cited by examiner

MONITORING HEART FAILURE

CROSS-REFERENCE TO RELATED APPLICATIONS

The present application is a continuation-in-part of international patent application PCT/EP04/08259 filed Jul. 23, 2004. The present application claims priority to, and benefit of, this application.

FIELD OF THE INVENTION

The present invention concerns a method for the detection of a predisposition to develop heart failure in patients with acute myocardial infarction, and also means for preventing the development of such heart failure. The method is qualitative and/or quantitative, and is adaptable to large-scale screening and clinical trials.

BACKGROUND

Over the last few decades, advances in the management of acute myocardial infarction (MI) have resulted in an impressive 40% reduction in mortality during the acute phase. However, despite these results, the development of late-onset heart failure following MI has not significantly decreased and remains associated with a more than 10-fold elevated risk of death. A better understanding of the factors involved in the development of late-onset heart failure will help to identify high-risk patients more likely to benefit from an intervention (Ref. 1-4).

Until recently, the initial laboratory evaluation of patients presenting myocardial infarction consisted entirely of creatine kinase (CK) and troponin measurements. Both are sensitive markers of myocardial injury and there is a reasonably good correlation between levels of CK and size of infarction in the absence of reperfusion. However, both markers are largely affected by a wash out phenomenon during reperfusion, which makes the interpretation of the markers difficult in the setting of thrombolysis and primary angioplasty/stenting, which are now the preferred mode of treatment of the majority of the patients with acute MI. Indeed, the relationship between levels of CK/troponin and the size of infarction or the risk for future cardiac events such as heart failure is inconsistent.

Several markers of inflammation such as high-sensitivity C-reactive protein (hs-CRP), soluble CD40 ligand and myeloperoxidase have been found to be independent predictors of death or nonfatal myocardial infarction at 6 months among patients presenting acute coronary syndromes. However, those markers have not been associated with the development of heart failure post MI. B-type natriuretic peptide (BNP) is a cardiac neurohormone that is elevated in response to left ventricular pressure overload. BNP is increasingly being recognized as an important prognostic marker in patients with heart failure and acute MI. The usefulness of BNP determination in the acute phase of MI is limited by rapid fluctuations in peptide levels during the first 24 hours of MI. BNP levels are also affected by numerous co-morbidities such as chronic obstructive lung disease and renal insufficiency.

The future management of patients with acute MI receiving reperfusion therapy with thrombolysis or primary angioplasty/stenting requires a strategy to more accurately risk-stratify patients and guide treatment. Accordingly it is an object of the present invention to provide a new technique for identifying subjects at risk of developing heart failure following a MI.

SUMMARY OF THE INVENTION

According to a first aspect of the present invention there is provided an in vitro method for identifying subjects at risk of heart failure following a Myocardial Infarction comprising analyzing the concentration of Matrix Metalloproteinase-9 in a bodily sample from a subject who has suffered a Myocardial Infarction and comparing this concentration with a reference for concentrations of Matrix Metalloproteinase-9 in individuals who have not suffered a Myocardial Infarction; wherein a raised concentration of Matrix Metalloproteinase-9 in the bodily sample from a subject who has suffered a Myocardial Infarction suggests that the patient is at risk of heart failure.

The method further provides an in vitro method for identifying Myocardial Infarction in patients suffering from chest pain or breathing trouble comprising analysing the concentration of Matrix Metalloproteinase-9 in a bodily sample from a subject. Hence, the method may therefore also be used to identify subjects suffering from Myocardial Infarction (MI), wherein a raised concentration of Matrix Metalloproteinase-9 (MMP-9) in the bodily sample suggests that the patient has or is suffering from MI. Conversely, a normal concentration of Matrix Metalloproteinase-9 excludes the presence of a Myocardial Infarction.

According to a second aspect of the invention, there is provided a kit for identifying a subject's risk of developing heart failure following a Myocardial Infarction, the kit comprising:
  (i) means for determining the concentration of Matrix Metalloproteinase-9 in a sample from a subject who has suffered a Myocardial Infarction; and
  (ii) a reference corresponding to the concentration of Matrix Metalloproteinase-9 in a sample from an individual who has not suffered a Myocardial Infarction wherein the kit is used to identify a raised concentration of Matrix Metalloproteinase-9 in the sample from the subject who has suffered a Myocardial Infarction compared to the reference concentration thereby suggesting that the subject who has suffered a Myocardial Infarction is at risk of developing heart failure.

According to a third aspect of the invention, there is provided a method of treating an individual having a risk of developing heart failure following a Myocardial Infarction, said method comprising the steps of: (i) determining the concentration of Matrix Metalloproteinase-9 in a sample having been obtained from a subject who has suffered a Myocardial Infarction, wherein a raised concentration of Matrix Metalloproteinase-9 in the bodily sample from the subject who has suffered a Myocardial Infarction compared to the concentration of Matrix Metalloproteinase-9 in a sample from an individual who has not suffered a Myocardial Infarction, suggests the subject who has suffered a Myocardial Infarction is at risk of developing heart failure; and (ii) administering to the subject who has suffered a Myocardial Infarction a therapeutic agent that prevents, reduces or delays progression of heart failure.

DEFINITIONS

Figure 1:
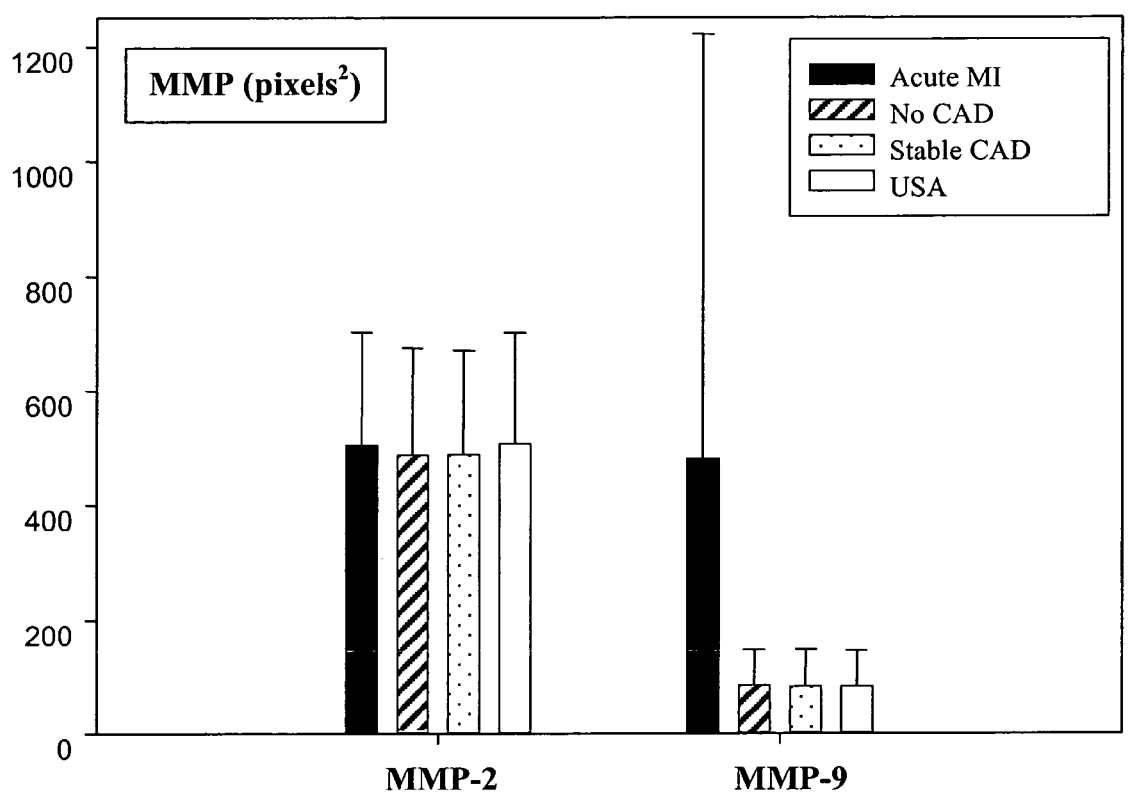
FIG. 1 illustrates levels of MMP-2 and MMP-9 determined by gelatin zymography in 109 patients with acute MI, 142 patients with atypical chest pain and normal coronary arteries (No CAD), 135 patients with stable coronary artery disease (stable CAD) and 53 patients with unstable angina (USA).

Before describing the present invention in greater detail, it is to be understood that this invention is not limited to particular devices, kits, or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

Myocardial Infarction (MI)

Acute myocardial infarction (MI) is a clinical syndrome in which a significant amount of the heart muscle eventually dies (necrosis). The primary event is an occlusive clot (thrombus) in a diseased coronary artery. If the thrombus is rapidly broken down by drugs (thrombolysis) or percutaneous coronary intervention with balloon angioplasty and stenting, part of the threatened heart muscle can be salvaged. More than 500000 patients are admitted annually in the US alone because of myocardial infarction. A significant proportion (>20%) will develop heart failure.

Heart Failure

Heart failure is the inability of the pumping heart muscle to meet the metabolic demands of the body. Its commonest cause is myocardial infarction where part of the heart muscle is replaced by scar. After symptoms are severe, 2-year mortality is 50% for patients with heart failure despite optimal medical therapy.

Metalloproteinase

Matrix metalloproteinases (MMPs) are a family of enzymes which participate in the degradation of extracellular matrix in the heart and other tissues. The extracellular matrix consists of a three-dimensional network of interstitial collagen to which other matrix components are attached. The main physiological function of this network is to retain tissue integrity and function. There are over 20 different MMPs.

DETAILED DESCRIPTION

The method according to the first aspect of the invention is useful for enabling a clinician to make decisions with regards the best course of treatment for a subject following an acute MI. In addition, the method of the first aspect is useful for monitoring the efficacy of a putative treatment for heart failure following myocardial infarction. Hence, the kit according to the second aspect is useful for providing a prognosis of the subject's condition, such that the clinician can carry out the treatment according to the third aspect. The kit can also be used to monitor the efficacy of a putative treatment for heart failure following myocardial infarction. The method and the kit are therefore very useful for guiding a treatment regime for the clinician, and to monitor the efficacy of such a treatment regime.

The inventor has realized that ventricular remodeling and recurrent MI are probably the most important mechanisms of late-onset heart failure following MI. The inventor has recognized that increased expression and activity of matrix metalloproteinases (MMPs—a family of Zinc dependent neutral metalloendopeptidases) occurs in human and animal hearts during the remodeling process after MI. In particular, peripheral levels of MMP-9 are elevated in patients with heart failure and acute coronary syndromes and targeted deletion of MMP-9 attenuates left ventricular dilation in the infarcted animal heart. The inventor therefore realized that MMP-9 is a useful physiological marker of left ventricular remodeling and heart failure in patients with acute myocardial infarction.

The inventor has determined that MMP-9 levels may be measured in patients with acute MI at the time of reperfusion and provide a useful estimate of the 2-year risk (following infarction) of developing left ventricular remodeling and heart failure.

Markers, which are currently measured in cardiac research include CPK, Troponin, hs-CRP, and pro-BNP. However, they cannot be used to predict heart failure post infarction because they are affected by the wash out phenomenon during reperfusion (CPK, Troponin). In addition, they are very unstable during the first 3 days post infarction due to transient changes in hemodynamics (pro-BNP). In addition, they are affected by other medical conditions such as infection (hs-CRP), COPD and renal disease (pro-BNP). In addition, most of these markers are analysed by determining their presence (or absence), and very rarely for their actual concentration. Accordingly, it is not possible to determine whether the concentration of these markers is raised or lowered compared to the 'normal' concentration in individuals who have not suffered an MI. Furthermore, most of theses markers only show whether there is any inflammatory response following the infarction, and not the ongoing repair process of the heart.

The inventor has established that circulating plasma levels of MMP-9 at the time of MI is suggestive of the two year risk of developing heart failure, which is often suffered after infarction, and often causes death. Accordingly, the method according to the first aspect of the invention, in which the concentration of MMP-9 is measured, provides a very reliable prognostic marker for monitoring the remodeling process of the heart, and also provides an indication as to the shape of the heart post infarction.

The subject may be any animal of veterinary interest and for whom post-MI management is relevant (for instance cats, dogs, horses etc). However, it is preferred that the subject is a human who has just suffered an MI.

Preferably, a sample is taken from the subject, and MMP-9 levels may measured within 1 week of an MI, preferably within 3 days of an MI and more preferably within 24 hours of an MI.

The sample may be any bodily sample into which MMP-9 is secreted (e.g. it may be lymph or interstitial fluid). The sample may be a urine sample. However, it is preferred that MMP-9 is measured or assayed in a blood sample. The blood sample may be venous or arterial. Blood samples may be assayed for MMP-9 levels immediately. Alternatively, the blood may be stored in a fridge or even frozen before the MMP-9 assay is conducted. Measurement of MMP-9 may be made in whole blood. However, in preferred embodiments of the invention, the blood may be further processed before an assay is performed. For instance, an anticoagulant, such as heparin, citrate, EDTA, and others may be added. Alternatively, the blood sample may be centrifuged to prepare a plasma or serum fraction for further analysis.

It will also be appreciated that "fresh" bodily samples may be analysed immediately after they have been taken from a subject. Alternatively the samples may be frozen (e.g. by dipping fresh samples in liquid nitrogen) and stored. The sample may then be defrosted and analysed at a later date.

MMP-9 may be assayed by a number of ways known to one skilled in the art. For example, immunoassays, such as the assays described in WO 00/20860, may be employed to measure MMP-9 levels. MMP-9 may also be determined with Western Blot analysis. Immunoassays and Western blot analyses assess the total protein level of MMP-9. However, neither immunoassays nor Western analysis is able to determine concentrations of the different forms (active or inactive) of MMP-9.

Accordingly, total MMP-9 enzyme concentration may be detected by enzyme-linked immunosorbent assay (ELISA), fluorometric assay, chemiluminescent assay, or radioimmunoassay.

However, a preferred method of measuring MMP-9 involves zymography analysis, and/or preferably, densitometry analysis (e.g. as described in the Example). With zymography, the concentration of the different forms (active & inactive) of MMP-9 is measured.

Zymography may comprise an electrophoresis step, a gel treatment step, and a staining step, and is then preferably followed by densitometry, as described in the Example. Zymography is a quantitative assessment of the concentration of MMP-9 (size of bands), and densitometry is a qualitative assessment of MMP-9 (density of bands). Accordingly, zymography and densitometry generate useful information not possible if using immunoassays or Western blots.

The inventor monitored the concentration of MMP-9 in more than 100 patients who had suffered an MI in a long term study (2 years), and compared them to the concentration of MMP-9 in more than 300 individuals who had not suffered from an MI. It will be appreciated that the concentration of MMP-9 in MI patients is highly dependent on how much time elapses between the time of the MI and the time when MMP-9 levels are assayed following MI. It will be appreciated that the concentration of MMP-9 in individuals who had not suffered from an MI does fluctuate to some degree, but that on average over a given period of time, the concentration tends to be substantially constant.

The inventor therefore noted that the average concentration of MMP-9 in individuals who had not suffered from an MI was <200 pixels$^2$ (as calculated using the method described in the Example), which corresponds to about 30 ng/ml. It will be appreciated that this is an average value and that a value falling somewhere between 10% above and 10% below the indicated value may be equally conclusive in the context of the present invention. This is referred to herein as the 'normal' concentration of MMP-9 and corresponds to the reference values discussed above. It will be appreciated that reference values may be obtained by assaying control samples (i.e. samples from subjects who have not suffered an MI). Alternatively reference values may be recorded on a data card. Accordingly, the reference (ii) according to the kit of the second aspect of the invention may be a control sample (for assaying) or in the form of a reference data card.

In addition, the inventor noted that the concentration of MMP-9 in those individuals who had suffered from an MI was >200 pixels$^2$ (as calculated using the method described in the Example). This is referred to herein as the 'raised' concentration of MMP-9. The inventor noticed that there is a direct relationship between MMP-9 levels and the risk of developing heart failure. The higher the MMP-9 concentration, the higher the risk. Using multivariate analysis, the inventor determined that the cut off value is log MMP-9=6.23. Above this MMP-9 level, patients have a 6.5-fold higher risk of developing heart failure.

A risk calculator may be put together in form of a chart and software for hand-held PCs. The risk calculator will estimate the 2-year risk of developing heart failure after myocardial infarction based upon the two strongest predictors in our study (i) MMP-9 level; and (ii) the history of a previous myocardial infarction. It is conceivable to include further clinical and biological risk markers in the risk calculator.

Accordingly, the inventor has realized that this difference in MMP-9 concentrations between the normal and raised levels, can be used as a physiological marker, suggestive of the two year risk of developing heart failure following an MI. It will be appreciated that if a subject has a raised concentration of MMP-9 which is considerably higher than the 'normal' MMP-9 concentration (for example, >300 pixels$^2$, >400 pixels$^2$, >500 pixels$^2$, >600 pixels$^2$), then they would be at a higher risk of developing heart failure within the two years following MI, then if the concentration of MMP-9 was only marginally higher then the 'normal' MMP-9 concentration (for example, between 200-300 pixels$^2$). Accordingly, a clinician would be able to make a decision as to the course of treatment required, for example, the type and dosage of therapeutic agent to be administered.

The majority of existing cardiac studies measure the presence or absence of markers, and not the actual concentration of the marker. Such methods rely on common ELISA detection and measurement technique instead of zymography, which determines the concentration of active MMP-9. The use of zymography is uncommon in such studies since it is very time consuming.

Advantageously, the concentration of active MMP-9 may be measured in the plasma of the individual who has suffered the myocardial infarction. It is known that other proteins play a role in heart failure post infarction, for example, phospholamban, SERCA, βARK. However, these proteins cannot be detected in the plasma of patients. In addition, it is surprising that there is a correlation between the concentration of MMP-9, and the two-year risk of developing further heart failure. Other proteins are known to play a role in heart failure, such as TNF-α, IL-6, and are elevated in the plasma of MI patients. However, there is no relationship between the concentration of these proteins, and prognosis of heart disease. Hence, measurement of TNF-α, IL-6, is not in clinical use.

The kit according to the second aspect may comprise suitable means for determining the concentration of Matrix Metalloproteinase-9 in the sample once this has been obtained from the subject. The detection means may comprise the use of antibodies coupled to a colorimetric method. In this case, the test will either be positive (high risk) or negative (low risk).

The kit may comprise a risk calculator incorporating the level of MMP-9 in form of a chart or a software program for traditional and/or a handheld PC. The risk calculator may comprise information concerning other risk factors, for example history of myocardial infarction, diabetes and age.

The risk calculator may comprise information concerning the level of MMP-9 and the presence or absence of a previous myocardial infarction.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Figure 3A:
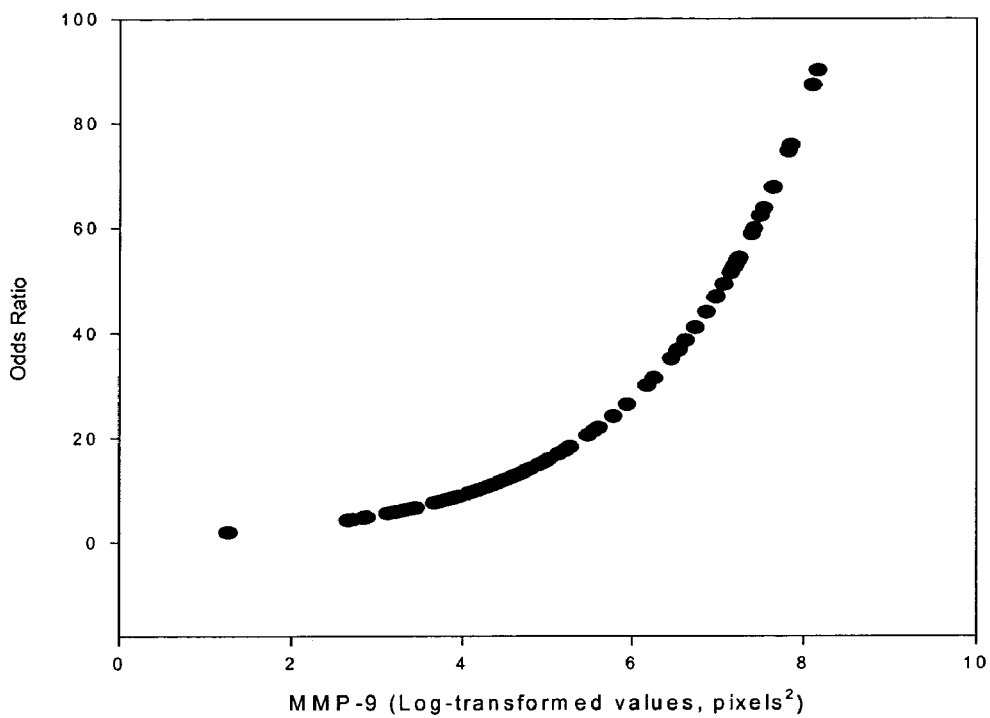
FIG. 3 illustrates the relationship between initial MMP levels (log transformed) and the risk, two years following MI, of: (A) developing heart failure NYHA class III-IV; and (B) having ejection fraction <40%.
Figure 3B:
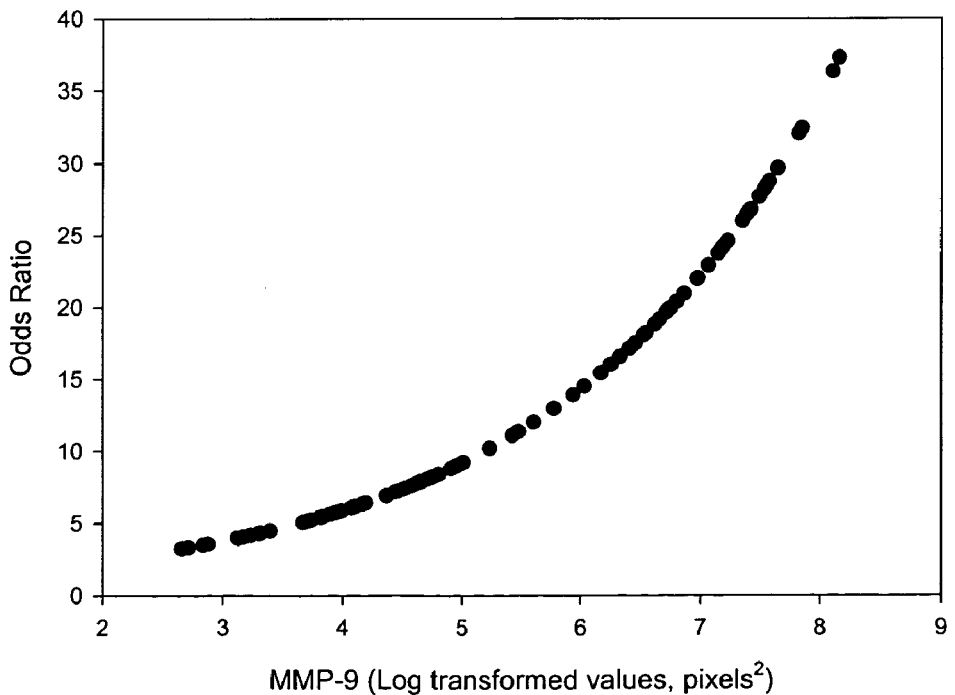

For a better understanding of the invention, and to show how embodiments of the same may be carried into effect, reference will now be made, by way of example, to the non-limiting Example and drawings, in which:

FIG. 1 illustrates levels of MMP-2 and MMP-9 determined by gelatin zymography in 109 patients with acute MI, 142 patients with atypical chest pain and normal coronary arteries (No CAD), 135 patients with stable coronary artery disease (stable CAD) and 53 patients with unstable angina (USA);

FIG. 2 illustrates: (A) Time course of MMP-9 levels in acute MI patients after reperfusion; and (B) Distribution of MMP-9 levels in patients with acute MI; and showing a biphasic pattern with a larger and a smaller peak. A kernel density procedure was used to evaluate the density at the specified points;

FIG. 3 illustrates the relationship between initial MMP levels (log transformed) and the risk, two years following MI, of: (A) developing heart failure NYHA class III-IV; and (B) having ejection fraction <40%; and

EXAMPLE

Experiments were conducted to illustrate that subjects with elevated levels of MMP-9 at the time of infarction are at high risk for the development of left ventricular remodeling and late onset heart failure during follow-up.

Methods

Study group. In the present study, 109 consecutive patients with acute MI (<24 hours) referred for primary coronary intervention (PCI) to the Centre Hospitalier Luxembourg/Institut National de Chirurgie Cardiaque et de Cardiologie Interventionnelle, were prospectively evaluated. Acute MI was defined by the presence of typical chest pain, the presence of significant ST-segment elevation in two or more ECG leads, and peak elevation of plasma creatine kinase to at least twice normal (400 U/L). All patients underwent coronary angioplasty and stenting with use of abciximab unless contraindicated. Blood samples were taken at the time of the PCI. Patients were followed in 6-month intervals for any major cardiac event or the development of heart failure class NYHA III-IV.

To evaluate left ventricular volumes and ejection fraction, long term survivors underwent a radionuclide ventriculography 2 years (mean of 24 months, 11-37 months) after the MI. Left ventricular ejection fraction (EF), end-diastolic volume (EDV) and end-systolic volume (ESV) were determined semi-automatically. The investigator reading the nuclear studies was unaware of the clinical status of the patients or their biological parameters. All patients signed informed consent and the study was approved by the local Ethics Committee.

Measurements. All blood samples were frozen at −70° C. until analysis. The activities of MMP-2 and MMP-9 were determined using zymography and densitometry analysis. Briefly, equal amounts of plasma (1 μl) were loaded on 10% SDS-polyacrylamide gel electrophoresis co-polymerized with gelatinase A and B (0.5 mg/ml each) as the substrates. Levels of high sensitivity C-reactive protein (hs-CRP) and pro-brain natriuretic peptide (pro-BNP) were measured with sandwich enzyme immunoassay. Tumor necrosis factor-α (TNF-α) was determined with enzyme linked immunosorbent assay.

Zymography. The purpose was to set up a zymographic analysis of matrix metalloproteinase 2 and 9, through its ability to cleave gelatine A and B, respectively. The process included an electrophoresis, a gel treatment and a staining step, followed by densitometry.

1) Electrophoresis 1-1 Set Up (i) Clean two glass plates with Ethanol 70%;

(ii) Clip them on the vertical holder;

(iii) Fill them up with distilled water to check that no leaking occurs.

1-2 Gel Casting

|  | Lower (running) 8% | Upper (stacking) 4% |
| --- | --- | --- |
| DD H$_2$O | 9.6 ml** | 12.34 ml |
| Gelatin | 20 mg* | / |
| Acrylamid/bis | 5.34 ml | 2.66 ml |
| Lower Tris | 5 ml | / |
| Upper Tris | / | 5 ml |
| SDS 10% | 200 μl | 200 μl |
| APS 10%*** | 100 μl | 100 μl |
| Temed*** | 10 μl | 20 μl |
| Volume final (4/gels) | 20 ml | 20 ml |

*For the preparation of gelatin A and B, weigh out 30 mg, and then solubilize them in 2 ml at 37° C. Then add the appropriate volume for the gel preparation.
**Substract these volumes to the water volume.
***Temed and persulfate must be added right before pouring the gels, as they allow the polymerization.

The running buffer was first poured up to 1 cm below the comb. 1 ml iso-butanol was quickly added to saturated in water. The gel was left for about 30 min to polymerise. The isobutanol was sucked with absorbing paper, and then washed with distilled water. The stacking gel was poured, and the comb was set being sure to avoid any air bubbles.

When the polymerization was complete (30 min), the comb was slowly removed, and then the wells were rinsed with running buffer.

1-3 Electrophoresis Procedure

The samples were prepared, on ice, with the Tris-glycine SDS sample buffer 2×. The standards were diluted to load the same volume, and then allowed to sit for 10 minutes before loading. The gels were set on the holder, and the reservoir was filled with running buffer. The samples and the molecular weight standards were loaded, as well as the positive MMP2 and MMP9 controls. The samples were allowed to migrate for 2 hours, with the voltage set at 100 V.

2) Gel Treatment (i) Renaturation—The gels were soaked under gentle shaking, three times for 20 minutes in 50 ml of renaturation buffer.

(ii) Development—The gels were rinsed with 10 ml development buffer. The gels were equilibrated with 50 ml of development buffer for 30 minutes at room temperature. The buffer was replaced with 50 ml new buffer, and incubated overnight at 37° C.

(iii) Staining—The gels were soaked for 15 minutes in staining solution.

(iv) Discolouration—The gels were soaked in discolouration buffer for 5 minutes.

(v) Contrast buffer—The gels were soaked in contrast buffer up to the moment they were dried.

3) Gel Analysis

Scanning procedure

Densitometry

4) Products

| | | |
|---|---|---|
| Gelatin A | From porcine skin | Sigma G-6144 |
| Gelatin B | From bovine skin | Sigma G-6650 |
| Acrylamid/bis | | Bio-rad 161-0158 |
| APS (Amonium persulfate) | | Bio-rad 161-0700 |
| SDS (lauryl sulphate) | | Sigma L-3771 |
| Temed | | Bio-rad 161-0800 |
| Running Buffer 10X (Tri-glycine-SDS) | | Bio-rad 161-0732 |
| Tris base | | Bio-rad 161-0715 |
| Glycerol | | Merck 1.04093.1000 |
| Glycine | | Sigma G-8898 |
| Triton X-100 | | Sigma T8532-500 ml |
| Brij 35 30% w/v | | Sigma diagnostics 430AG6 |
| NaCl | | VWR 1723 |
| $CaCl_2$ | | Merck 2381.100 |
| Bromophenol blue | | Sigma B-7021 |

5) Buffers

| Lower Tris (1.5M Tris-HCl, pH 8.8) | |
|---|---|
| Tris base | 18.15 g |
| Distilled water | 70 ml |
| Adjust to pH 8.8 with HCl 12 N | |
| Adjust to 100 ml with distilled water | |
| Store at 4° C. | |

| Upper Tris (0.5M Tris-HCl, pH 6.8) | |
|---|---|
| Tris base | 6 g |
| Distilled water | 70 ml |
| Adjust to pH 6.8 with HCl 12 N | |
| Adjust to 100 ml with distilled water | |
| Store at 4° C. | |

| Loading Buffer 2X: | |
|---|---|
| 0.5M Tris-HCl, pH 6.8 | 2.5 ml |
| Glycerol | 2 ml |
| SDS 10% | 4 ml |
| 0.1% Bromophenol blue | 0.5 ml |
| Adjust with distilled water to | 10 ml |

| Running Buffer (10X): | |
|---|---|
| Tris Base | 29 g |
| Glycine | 144 g |
| SDS | 10 g |
| Adjust with distilled water to | 1000 ml |

| Renaturing Buffer (10X): | |
|---|---|
| 2.5% Triton X-100 in distilled water | |

| Developing Buffer (10X): | |
|---|---|
| Tris 0.5M, Brij 35 0.2%, NaCl 2M, $CaCl_2$ 50 mM, pH 7.6 | |
| Tris | 30.2 g |
| Brij 30% w/v | 3.3 ml |
| NaCl | 58.4 g |
| $CaCl_2$ | 3.6 g |
| Adjust to pH 7.6 with HCl 12N | |
| Adjust to 500 ml with distilled water. | |
| Store at 4° C. | |

| Staining: | |
|---|---|
| 40% v/v Methanol, 10% v/v acetic acid, 0.1% w/v Coomassie blue | |
| Methanol | 200 ml |
| Acetic acid | 50 ml |
| Coomassie blue | 0.5 g |
| Adjust to 500 ml with distilled water. | |

| Discolouration: | |
|---|---|
| 30% v/v Methanol, 10% v/v acetic acid | |
| Methanol | 150 ml |
| Acetic acid | 50 ml |
| Adjust to 500 ml with distilled water | |

| Contrast buffer: | |
|---|---|
| 5% v/v Glycerol, 10% v/v acetic acid | |
| Glycerol | 25 ml |
| Acetic acid | 50 ml |
| Adjust to 500 ml with distilled water | |

Characterization of MMPs. In order to better define peripheral levels of MMPs, the inventor performed additional studies. First, the inventor measured levels of MMP-2 and MMP-9 on day 0, day 1 and day 3 in patients with acute MI (n=20) to assess the time course of MMP release post MI. Second, the inventor measured MMP-2, MMP-9, hs-CRP and TNF-α in consecutive patients without MI undergoing coronary angiography who presented with unstable angina (n=53), stable angina (n=135) or atypical chest pain with normal coronary arteries (n=142). Third, the inventor measured levels of MMP-9 at 3-months intervals in patients with stable CHF (n=15).

Statistical Analysis

Descriptive statistics were produced as means, standard deviations and percentages as appropriate to describe the studied population. One-way anova was used to compare mean values between observed groups of patients defined by a qualifying event (i.e. Groups defined by a follow-up NYHA score of III-IV or ejection fraction of <40%). In case of a significant Shapiro-Wilk test for normal data, a non-parametric Mann-Withney test was used. Linear regression and correlation were performed to study the relationship between biological predictors. A logistic regression model was used to investigate the association of the NYHA score at 2-year with patients characteristics and biological predictors. Then a logistic regression model was used to model ejection fraction ($\leq 40\%$, >40%) at 2-year with patient characteristics and biological predictors.

Model building proceeded with stepwise backward elimination, requiring p<0.05 for significance, starting with a model that contained all variables. After final selection, variable interactions were tested following the same method. Wald chi-squared test and Likelyhood ratio test were used to assess the significance of variables in the model. A p-value of <0.05 was considered statistically significant. All tests were two-tailed. Statistical analyses were carried out with the statistical package Intercooled Stata version 7.0 (Stata Corporation, College Station, Tex., USA).

Results

The baseline clinical characteristics of patients with and without CHF development during follow-up are summarized in Table 1. Of the 109 patients with acute MI, 11 patients died and 15 patients developed heart failure NYHA class III-IV during 2 year follow-up. Seven patients were lost during follow-up.

TABLE 1

CLINICAL CHARACTERISTICS OF PATIENTS WITH AND WITHOUT THE DEVELOPMENT OF HEART FAILURE IN SURVIVORS OF MI

|  | No CHF (N = 76) | CHF (N = 15) | p-value |
|---|---|---|---|
| Demographics |  |  |  |
| Age (Years) | 57 ± 12 | 62 ± 15 | 0.15* |
| Male | 60 (66%) | 9 (10%) | 0.12¥ |
| BMI (kg/m²) | 27.8 ± 4.3 | 28.9 ± 4.5 | 0.36* |
| Risk factors |  |  |  |
| Diabetes | 13 (14.3%) | 4 (4.4%) | 0.38# |
| Hypertension | 25 (27.5%) | 9 (9.9%) | 0.05¥ |
| Hypercholesterolemia | 38 (41.7%) | 6 (6.6%) | 0.48¥ |
| Current smoker | 41 (45.1%) | 6 (6.6%) | 0.32¥ |
| Cardiovascular history |  |  |  |
| Previous MI | 19 (20.9%) | 6 (6.6%) | 0.23¥ |
| Previous PCI | 11 (12.1%) | 2 (2.2%) | 1.00# |
| Previous CABG | 0 (0%) | 0 (0%) |  |
| Medications at presentation |  |  |  |
| ACE inhibitors | 15 (16.8%) | 6 (6.6%) | 0.09¥ |
| Beta-blockers | 30 (32.9%) | 5 (5.5%) | 0.65¥ |
| Aspirin | 49 (53.85%) | 5 (5.5%) | 0.02¥ |
| Nitrates | 19 (20.9%) | 4 (4.4%) | 1.00# |
| Diuretics | 3 (3.3%) | 0 (0%) | 1.00# |
| Calcium-channel blocker | 5 (5.5%) | 0 (0%) | 0.59# |
| Clopidogrel | 16 (17.6%) | 0 (0%) | 0.06# |
| Statins | 20 (21.9%) | 1 (1.1%) | 0.18# |

In Table 1:
*One way analysis of variance,
‡Non-parametric Mann-Withney test,
¥Chi2 test,
Fisher Exact Chi2 test.
MI, myocardial infarction;
PCI, percutaneous coronary intervention;
CABG, coronary artery bypass grafting;
ACE, angiotensin-converting enzyme Parameters at the Time of Reperfusion Levels of MMP-2 were not increased in patients with acute MI, as illustrated in FIG. 1. However, as can be seen in FIG. 1, in contrast to MMP-2, levels of MMP-9 were significantly increased at the time of reperfusion (p<0.001). Patients with stable or unstable coronary artery disease did not show any elevation of MMP-9. Levels of hs-CRP were 4.6-fold increased in patients with acute MI when compared to patients without coronary artery disease (p<0.001). Interestingly, there was no correlation between MMP-9 and hs-CRP (p=0.23). Similarly, pro-BNP was found to be augmented in patients with acute MI without any correlation with MMP-9 levels (p=0.92). However, levels of MMP-9 correlated with levels of CPK (p<0.0001) and TNF-α (p=0.005). This was a first indication that MMP-9 may be related to the size of the infarction.

Figure 2A:
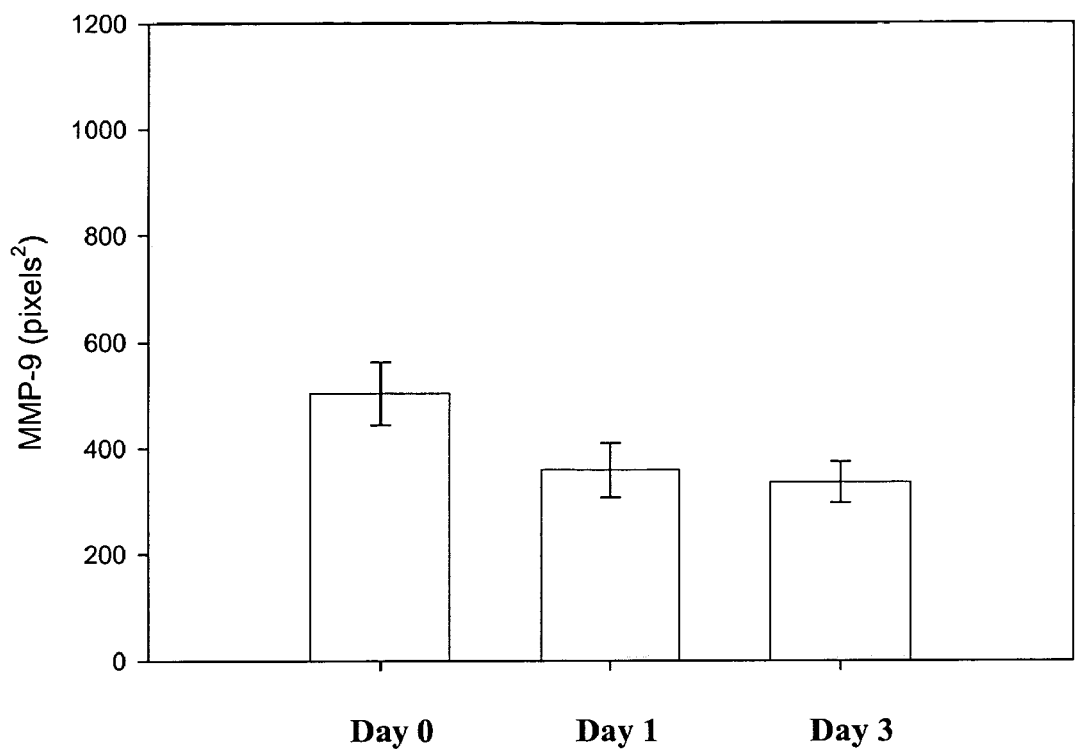
FIG. 2, Panels A and B illustrates: (A) Time course of MMP-9 levels in acute MI patients after reperfusion; and (B) Distribution of MMP-9 levels in patients with acute MI; showing a biphasic pattern with a larger and a smaller peak. A kernel density procedure was used to evaluate the density at the specified points.
Figure 2B:
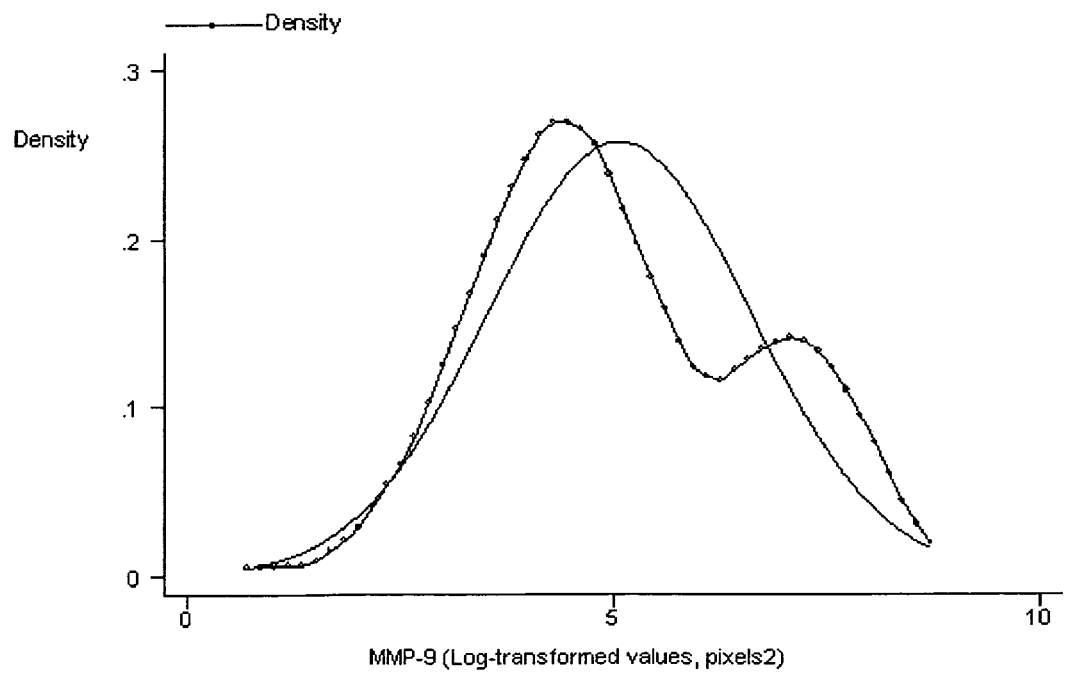

The inventor recorded maximal levels of MMP-9 at the time of initial presentation which, in our study, corresponded to the first 24 hours after onset of symptoms, as illustrated in FIG. 2A. Thereafter, MMP-9 slowly declined. The inventor observed a biphasic distribution of MMP-9 values among the acute MI patients with a first major peak and a second smaller peak, as illustrated in FIG. 2B. The group of patients with stable CHF without MI and with EF<40% had elevated levels of MMP-9 which did not vary significantly of the course of 3 months (data not shown).

Multivariate Predictors of Late Onset CHF

As shown in Table 2, patients with high levels of MMP-9 at the time of infarction were more likely to develop heart failure during their post MI course. Indeed, NYHA functional class at 2-year follow-up was higher in patients with elevated initial MMP-9 (p<0.02). This was independent of treatment with beta-blockers or angiotensin converting enzyme inhibitors. Using a multi-variate analysis, we established that patients with high initial MMP-9 levels (above the cut off value of Log MMP-9=6.23), had an OR of 6.5 (95% CI 1.7-25.3, p<0.006) of developing late onset heart failure class III-IV. The impact of MMP-9 on the development of heart failure after MI is shown in FIG. 3.

TABLE 2

Biological predictors of late onset heart failure post MI

|  | No CHF at 2 years (n = 76) | CHF class III-IV at 2 years (n = 15) | p |
|---|---|---|---|
| CARDIAC FUNCTION AT 2 YEARS ||||
| EF (%) | 52.5 ± 11.4 | 43.1 ± 9.4 | 0.03* |
| EDV (ml) | 80.3 ± 25.2 | 93.5 ± 20.2 | 0.03** |
| ESV (ml) | 40.9 ± 25.0 | 54.9 ± 19.8 | 0.04* |
| Circulating factors at time of MI ||||
| TNF (pg/ml) | 1.7 ± 1.6 | 2.1 ± 1.9 | 0.44 |
| Pro-BNP (pg/ml) | 982 ± 2290 | 2138 ± 4637 | 0.39 |
| CRP (mg/dl) | 2.0 ± 3.2 | 2.6 ± 4.2 | 0.82 |
| CPK max | 1561 ± 1477 | 2534 ± 1676 | 0.08 |
| MMP-2 (pixels²) | 463 ± 176 | 600 ± 261 | 0.06 |
| MMP-9 (pixels²) | 493 ± 810 | 983 ± 640 | 0.02** |

In Table 2:
Patients with acute MI (n = 109) were followed for the development of CHF and cardiac function was assessed with radionuclide ventriculography at 2 years.
Circulating factors were measured at the time of MI and compared between patients with and without development of CHF.
*One way analysis of variance.
**Non-parametric Mann-Withney test.
CHF, congestive heart failure,
EF, ejection fraction,
EDV, enddiastolic volume,
ESV, endsystolic volume,
TNF, tumor necrosis factor-α,
BNP, brain natriuretic peptide,
CRP, C-reactive protein,
CPK, creatine kinase,
MMP, matrix metalloproteinase.

These results were corroborated by the measurements of cardiac volumes and function at 2 year follow up, as illustrated in Table 2 and in FIG. 3. Indeed, patients with high initial MMP-9 levels were more likely to develop left ventricular dysfunction (EF % 43±9 vs. 52±11, p<0.03) and remodeling. The impact of initial MMP-9 levels on EF is depicted in FIG. 3. All other biological parameters determined in the present study (TNF-α, pro-BNP, hs-CRP, creatine kinase and MMP-2) were also slightly higher in patients that would later develop heart failure (Table 2). However, the difference was not statistically significant and multivariate analysis did only identify MMP-9 as a predictor of late onset heart failure post MI.

It is noteworthy that patients with a history of MI had an OR of 5.6 (95% CI 1.3-24.3, p=0.02) of developing late onset heart failure following MI. Multivariate analysis also identified a history of aspirin intake at presentation as a protective factor against the development of heart failure (OR of 0.15, 95% CI 0.04-0.6, p=0.007).

Discussion

These data illustrate that patients with elevated levels of MMP-9 at the time of infarction have a high risk for heart failure following an MI (most likely as a result of left ventricular remodeling). Measurement of MMP-9 levels represents a better risk indicator of patients at risk of heart failure, following MI, than pro-BNP, TNF-α, hs-CRP or creatine kinase. Indeed, a single determination of MMP-9 at the time of reperfusion therapy was able to determine patients at high risk (OR of 6.5) for the development of late onset heart failure NYHA class III-IV and EF<40%.

The successes of modern reperfusion therapies have resulted in an increasing proportion of infarct survivors (Ref. 1-4). However, the risk of developing CHF post MI has not decreased, and will likely increase as the proportion of survivors will further be augmented by the implantation of automatic defibrillators (Ref 11). Therefore, CHF following MI remains a major problem. Patients who develop CHF days after MI have a high in-hospital mortality rate. Little is known, however, about the predictors of late onset CHF (years) after MI. Analysis of the CARE study has revealed that the most important clinical predictors of late onset CHF post MI are age, EF, diabetes, hypertension and previous MI. A history of MI was also an important predictor of late onset CHF in our study. Some of these factors are similar to predictors of acute CHF after MI such as age and diabetes.

Among the circulating factors reflecting left ventricular function, pro-BNP is increasingly being recognized as an important prognostic marker in patients with heart failure and acute MI (Ref. 12-15). The results of elevated levels of pro-BNP in patients with acute MI confirm those reports. Of note, previous studies evaluating pro-BNP in acute MI have included very few patients with primary angioplasty and stenting. Furthermore, the usefulness of BNP determination in the acute phase of MI is limited by rapid fluctuations in peptide levels during the first 24 hours of MI. BNP levels are also affected by numerous co-morbidities such as chronic obstructive lung disease and renal insufficiency.

The results are consistent with the reported finding that peripheral levels of MMP-9 increase two- to three-fold following myocardial infarction (Ref. 5-10). The inventor observed a correlation between creatine kinase and MMP-9 levels. This fact may be due to a smaller, heterogeneous patient population with only 9 patients receiving reperfusion therapy, compared to our acute MI group, where all patients underwent coronary angioplasty and stenting, in the majority with the use of abciximab.

This is the first report demonstrating that MMP-9 is a powerful independent predictor of left ventricular remodeling and CHF following MI. Early postmyocardial plasma MMP-9 levels had a significant inverse relation with left ventricular size and function at 2 years. This was not the case for creatine kinase or pro-BNP. This is potentially explained by the fact that MMP-9 may be less affected by the wash out phenomenon and transient hemodynamic changes at the time of reperfusion, which complicate the interpretation of creatine kinase and pro-BNP levels. In studies by Omland et al. and Richards et al., only about half of the patients received reperfusion therapy with thrombolysis and BNP levels were determined on day 2 to 4 after the MI when peptide levels are in a steady state.

So far, clinical studies investigating MMP-9 levels concluded that elevated levels were due to the process of coronary artery plaque rupture. However, in view of recent animal studies, it appears more likely that neutrophils infiltrating the infarcted myocardium are the major source of MMP-9 in the setting of acute MI (Ref. 16-17). MMP-9 probably acts directly on the myocardium as a protease and facilitates neutrophil infiltration and degranulation, exacerbating the ischemic insult. This may explain why MMP-9 appears to be an accurate marker for the extent of the injury. Several investigators have sought to understand the potential therapeutic benefits of MMP inhibition. For instance, observations in the TNF-α transgenic mouse model indicate that MMP inhibition has a narrow window of opportunity in the early phase of remodeling. Indeed, MMP inhibition had no beneficial effect on ventricular size and function in old mice with established CHF.

Many cytokines, including TNF-α and transforming growth factors, induce MMP expression. In the present study, peripheral levels of TNF-α were only mildly elevated at the time of myocardial infarction. Nevertheless, there was a positive correlation between levels of MMP-9 and TNF-α which is in accordance with the notion that the cytokine cascade is initiated by TNF-α during myocardial injury.

In contrast to previous reports, the inventor did not observe an elevation of MMP-2 levels at the time of MI. The difference between this study and the prior art may possibly be related to a different analytical technique. Using zymography, the inventor measured enzymatic activity of MMPs, which reflects the biological state whereas immunoassays used in the previous study do not distinguish between the active and inactive proenzyme form of MMPs.

In conclusion, MMP-9 is a robust and very early marker of left ventricular remodeling in patients with acute MI and particularly those treated with primary angioplasty and stenting. Therefore MMP-9 is useful as a prognostic marker according to the present invention and may be used to guide treatment and to prove the presence of myocardial infarction.

REFERENCES

1. Guidry U C, Evans J C, Larson M G, et al. *Circulation*: 1999;100:2054-2059.
2. Lewis E F, Moye L A, Rouleau J L, et al. *J Am Coll Cardiol* 2003;42:1446-1453.
3. Pfeffer M A, Braunwald E. *Circulation* 1990;81:1161-1172.
4. Frangogiannis N G, Smith C W, Entman M L. *Cardiovasc Res* 2002;53:31-47.
5. Creemers E E J M, Cleutjens J P M, Smits J F M, et al. *Circ Res* 2001;89:201-210.
6. Wilson E M, Gunasinghe H R, Coker M T, et al. *J Cardiac Failure* 2002;8;390-398.
7. Altieri P, Brunelli C., Garibaldi S et al. *Eur J Clin Invest* 2003;33:648-656.
8. Kai H, Ikeda H, Yasukawa H, et al. *J Am Coll Cardiol* 1998;32:368-372.
9. Inokubo I, Hanada H, Ishizaka H, et al. *Am Heart J* 2001;141:211-217.
10. Rohde L E, Ducharme A, Arroyo L H, et al. *Circulation* 1999;99:3063-3070.
11. Moss A J, Zareba W, Hall W J, et al. *N Engl J Med* 2002;346;877-883.
12. O'Connor C M, Hathaway W R, Bates E R, et al. *Am Heart J* 1997;133:663-673.
13. Anand I S, Fisher L D, Chiang Y T, et al. *Circulation* 2003;107:1278-1283.

14. Omland T, Aakvaag A, Bonarjee V V S, et al. *Ciculation* 1996;93:1963-1969.
15. Richards A M, Nicholls M G, Yandle T G, et al. *Circulation* 1998;97:1921-1929.
16. Lindsey M, Wedin K, Brown M D, et al. *Circulation* 2001;103:2181-2187.
17. Romanic A M, Harrison S M, Bao W, Burns-Kurtis C L, Pickering S, Gu J, Grau E, Mao J, Sathe G M, Ohlstein E H, Yue T L. *Cardiovasc Res* 2002;54:549-558.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An in vitro method for identifying a relative risk of heart failure in a subject following a Myocardial Infarction compared to subjects who have not suffered a Myocardial Infarction, the method comprising:
    determining a concentration of Matrix Metalloproteinase-9 in a bodily fluid sample from a subject who has suffered a Myocardial Infarction wherein said concentration of Matrix Metalloproteinase-9 is determined within twenty-four hours of said Myocardial Infarction;
    comparing the concentration of Matrix Metalloproteinase-9 in said subject following Myocardial Infarction with a reference concentration of Matrix Metalloproteinase-9 from individuals who have not suffered a Myocardial Infarction; and,
    correlating the concentration of Matrix Metalloproteinase-9 to a relative likelihood of heart failure wherein the concentration of Matrix Metalloproteinase-9 in the subject's sample is predictive for the relative risk that the subject will develop heart failure two years following Myocardial Infarction.

2. The method according to claim 1, wherein the sample is a blood sample or a urine sample.

3. The method according to claim 2, wherein the blood or urine sample is analysed immediately after it is taken from the subject.

4. The method according to claim 2, wherein the blood or urine sample is frozen and stored before being defrosted and analysed.

5. The method according to claim 1, wherein the concentration of Matrix Metalloproteinase-9 is measured by zymography.

6. The method according to claim 5, wherein the zymography comprises an electrophoresis step, a gel treatment step, and a staining step.

7. The method according to claim 1, wherein the concentration of Matrix Metalloproteinase-9 is measured by zymography and densitometry.

8. The method according to claim 1, wherein the concentration of Matrix Metalloproteinase-9 is measured by an enzyme-linked immunosorbent assay (ELISA), fluorometric assay, a chemiluminescent assay, or a radioimmunoassay.

9. The method according to claim 1, wherein the sample is a blood sample and wherein the raised concentration of Matrix Metalloproteinase-9 is higher than 30 ng/ml or 200 pixels$^2$.

10. A kit for identifying a subject's relative risk of developing heart failure following a Myocardial Infarction, the kit comprising:
    (i) means for determining a concentration of Matrix Metalloproteinase-9 in a bodily fluid sample from a subject who has suffered a Myocardial Infarction; and,
    a risk calculator that calculates the subject's relative risk of developing heart failure two years following Myocardial Infarction based upon the concentration of Matrix Metalloproteinase-9 in a bodily fluid sample from the subject.

* * * * *

UNITED STATES PATENT AND TRADEMARK OFFICE
CERTIFICATE OF CORRECTION

PATENT NO.        : 7,319,017 B2                          Page 1 of 1
APPLICATION NO.   : 11/181675
DATED             : January 15, 2008
INVENTOR(S)       : Daniel R. Wagner et al.

It is certified that error appears in the above-identified patent and that said Letters Patent is hereby corrected as shown below:

On the title page item 73 titled "Assignee", please replace:

"Centre de Recherche Public de la Santé, Luxembourg (LU)" with --Luxembourg Institute of Health, Luxembourg (LU)--

Signed and Sealed this
Thirty-first Day of May, 2016

Michelle K. Lee
*Director of the United States Patent and Trademark Office*